US008452616B1

(12) United States Patent
Soong

(10) Patent No.: US 8,452,616 B1
(45) Date of Patent: *May 28, 2013

(54) SYSTEMS AND METHODS FOR PATIENT RECORDS MANIPULATION

(76) Inventor: James W. Soong, Redondo Beach, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 12/798,897

(22) Filed: Apr. 13, 2010

Related U.S. Application Data

(63) Continuation of application No. 11/112,468, filed on Apr. 23, 2005, now Pat. No. 7,725,332, which is a continuation of application No. 09/500,977, filed on Feb. 15, 2000, now Pat. No. 6,941,271.

(51) Int. Cl.
G06Q 50/00 (2006.01)

(52) U.S. Cl.
USPC ............................... 705/3; 707/783; 600/300

(58) Field of Classification Search
USPC .......................................... 705/2–4; 707/783
See application file for complete search history.

(56) References Cited

U.S. PATENT DOCUMENTS

| 4,878,175 | A |   | 10/1989 | Norden-Paul et al. ............. 705/2 |
| 5,084,828 | A | * | 1/1992  | Kaufman et al. .............. 700/242 |
| 5,544,044 | A | * | 8/1996  | Leatherman ....................... 705/3 |
| 5,633,910 | A | * | 5/1997  | Cohen ............................. 379/38 |
| 5,754,111 | A |   | 5/1998  | Garcia ......................... 340/573.1 |
| 5,772,585 | A |   | 6/1998  | Lavin et al. .................... 600/300 |
| 5,785,650 | A | * | 7/1998  | Akasaka et al. .............. 600/300 |
| 5,924,074 | A | * | 7/1999  | Evans ............................... 705/3 |
| 5,974,389 | A |   | 10/1999 | Clark et al. ........................ 705/3 |
| 5,997,476 | A |   | 12/1999 | Brown ............................ 600/300 |
| 6,024,699 | A | * | 2/2000  | Surwit et al. .................... 600/300 |
| 6,032,119 | A | * | 2/2000  | Brown et al. ....................... 705/2 |
| 6,073,106 | A |   | 6/2000  | Rozen et al. ...................... 705/3 |
| 6,076,166 | A |   | 6/2000  | Moshfeghi et al. ............. 713/201 |
| 6,112,209 | A | * | 8/2000  | Gusack ............................... 1/1 |
| 6,208,974 | B1 |  | 3/2001  | Campbell et al. .................. 705/3 |
| 6,277,072 | B1 | * | 8/2001  | Bardy ............................ 600/300 |
| 6,302,844 | B1 | * | 10/2001 | Walker et al. .................. 600/300 |
| 6,304,788 | B1 |  | 10/2001 | Eady et al. ........................ 700/86 |
| 8,302,844 | B2 |  | 10/2001 | Walker el al. .................. 600/300 |
| 6,322,502 | B1 |  | 11/2001 | Schoenberg et al. ........... 600/300 |
| 6,347,329 | B1 |  | 2/2002  | Evans ............................ 709/202 |
| 6,463,417 | B1 |  | 10/2002 | Schoenberg ....................... 705/2 |

(Continued)

FOREIGN PATENT DOCUMENTS

WO        WO 9732271 A1        9/1997

OTHER PUBLICATIONS

Safran C. et al., A clinical trial of a knowledge-based medical record, MEDINFO, 1995, p. 1076-1080. File 155, # 12922796.

(Continued)

Primary Examiner — Gerald J. O'Connor
Assistant Examiner — Sind Phongsvirajati

(57) ABSTRACT

A site computer includes a database for manipulating and handling health care records. A communication device, coupled to the site computer and the database, receives commands, which are provided to the site computer and the database to perform various functions, including creating, displaying, modifying, and initiating organization of the health care records. The health records can be automatically transmitted to interested persons upon creation of the health records. Upon detection of the occurrence of threshold events as indicated in the health records, the site computer automatically transmits notifications to interested persons.

20 Claims, 11 Drawing Sheets

U.S. PATENT DOCUMENTS

| | | | |
|---|---|---|---|
| 6,516,315 B1 * | 2/2003 | Gupta | 1/1 |
| 6,523,009 B1 | 2/2003 | Wilkins | 705/3 |
| 6,594,634 B1 * | 7/2003 | Hampton et al. | 705/3 |
| 6,602,469 B1 | 8/2003 | Maus et al. | 422/68.1 |
| 6,832,212 B1 * | 12/2004 | Zenner et al. | 705/40 |
| 6,965,917 B1 | 11/2005 | Aloni et al. | 709/206 |
| 7,013,298 B1 * | 3/2006 | De La Huerga | 1/1 |
| 7,016,856 B1 * | 3/2006 | Wiggins | 705/2 |
| 2001/0032100 A1 | 10/2001 | Mahmud et al. | 705/2 |
| 2003/0177030 A1 * | 9/2003 | Turner et al. | 705/2 |

OTHER PUBLICATIONS

Safran C. el al., Development of a knowledge-based electronic patient record, MD-Computing, Jan.-Feb. 1996, vol. 13, No. 1, p. 46-54, File 2. # 5234499.

Sterling commerce announces newest version of Connect: Remote, Featuring Advanced managed client capabialies, PR Newswire, Sep. 21. 1998, File 20, # 02877899.

* cited by examiner

PATIENT ID: ⎯⎯⎯⎯ 502
ID NUMBER: ⎯⎯⎯⎯ 504
DATE OF VISIT: ⎯⎯⎯⎯ 506
TREATMENT: ⎯⎯⎯⎯ 508
CONDITION: ⎯⎯⎯⎯ 510
OBSERVATIONS: ⎯⎯⎯⎯ 512
COSTS: ⎯⎯⎯⎯ 514
PREPARER/PROFESSIONAL: ⎯⎯⎯⎯ 516
ACCESS CODE NUMBER: ⎯⎯⎯⎯ 518

FIG. 5

SYSTEMS AND METHODS FOR PATIENT RECORDS MANIPULATION

The present application is a continuation application of application Ser. No. 11/112,468, filed Apr. 23, 2005 now U.S. Pat. No. 7,725,332, which is a continuation application of then application Ser. No. 09/500,977, filed Feb. 15, 2000 now U.S. Pat. No. 6,941,271, the disclosures of which are hereby incorporated by reference.

FIELD OF THE INVENTION

The present invention relates to the home health care industry and, in particular, to manipulation and handling of health care records to enhance patient care.

BACKGROUND

Health care providers perform myriad services in the treatment of the ill. The performance of such services is often documented in varying degrees of detail to serve various purposes. The condition and response of patients who receive health care services are also documented. For example, records are often kept in regard to each instance that service is rendered so that the course of treatment for the patient can be readily accessible if and when needed to, for example, assess the history and effectiveness of the treatment. As another example, health care professionals will periodically document the health condition of patients to gauge their progress under medical supervision or to simply assess their overall general health. As still another example, records are kept for legal purposes so that the health care provider can document that patients in their care have received proper care. There are other motivations for documenting the treatment of patients by health care providers.

The precise method of documenting rendered health care services and condition of patients during the course of treatment of patients is similar in many respects from one health care industry to the next. However, considerations of convention and necessity particular to each industry cause differences in the creation and maintenance of medical records. The home health care industry is an example.

The home health care industry plays a vital role in the treatment of persons who receive care at home or some other non-institutional setting. Typically, a nurse or other qualified health care professional will visit a patient in her home to provide some degree of care and assessment. Each visit will prompt the nurse to enter a description of services rendered for the patient, a description of the condition of the patient, and any other observations or determinations that, if documented, would potentially benefit the patient's welfare or serve some other constructive purpose. Descriptions or determinations of this kind can often serve as medical or health records of the patient.

Conventionally, access to health records has been traditionally limited. For example, too often the health care professional who renders care for the patient creates a record and retains the record without sharing the record with the home health care agency for whom the professional works. Such exclusive retention can cause administrative and accounting difficulties for an agency. Furthermore, such exclusive retention may preclude the patient, or other interested individual, from obtaining a comprehensive account of the patient's health history. Such preclusion may result in various drawbacks, varying from inconvenience to the patient, or home health care agency, to harm to the patient's welfare. It will be appreciated that an innovative technique to allow ready, yet secure, access to a patient's care history is needed.

SUMMARY OF THE INVENTION

Systems, methods, and computer readable media provide for manipulation of patient records. In an embodiment, records including types of data concerning a patient may be stored. Access rules to selectively control electronic access to the types of data may be received, the access rules determined by the patient. Access to the types of data may be controlled by applying the access rules determined by the patient. Access to a first type of data concerning the patient may be provided to a first group of individuals according to the access rules determined by the patient. Access to a second type of data concerning the patient may be provided to a second group of individuals according to the access rules determined by the patient. An indication from the patient of about a threshold event relating to data about the patient may be received. Occurrence of the threshold event may be determined by comparing a numerical value indicative of a condition of the patient with a threshold value indicative of associated with the threshold event. A notification to an entity selected by the patient may be provided in response to the occurrence of the threshold event, wherein the selected entity is not the patient, the threshold event and the notification relating to the first type of data. The notification may be withheld from the second group of individuals.

These and various other embodiments of the present invention, as well as the advantages and features of all of its many embodiments, are described in more detail in conjunction with the text below and attached figures.

BRIEF DESCRIPTION OF THE DRAWINGS

FIG. 5 shows a record page in accordance with one of many embodiments of the present invention;

DETAILED DESCRIPTION OF THE SPECIFIC EMBODIMENTS

In accordance with the present invention, a system and method for selective record creation and access allows for secure and convenient creation of, access to, modification of, manipulation and handling of, and transmission of records over a communications network. The present invention will be described in connection with and is particularly suited to records of a patient's health history during the rendering of home health care for the patient. However, it will be appreciated that the present invention can be used in other contexts as well. For example, the present invention would apply equally to medical or health records of a patient who receives other kinds of care besides home health care. In this regard, the invention applies also to, for example, hospital, institutional, clinical, or any other kind of medical, health, psychiatric, psychological, or other kind of care. Furthermore, the present invention applies to contexts completely outside the health care industry altogether. In this regard, the present invention applies to records kept, maintained, or organized during any process that involves creating records of the status and progress of the process.

Figure 1:
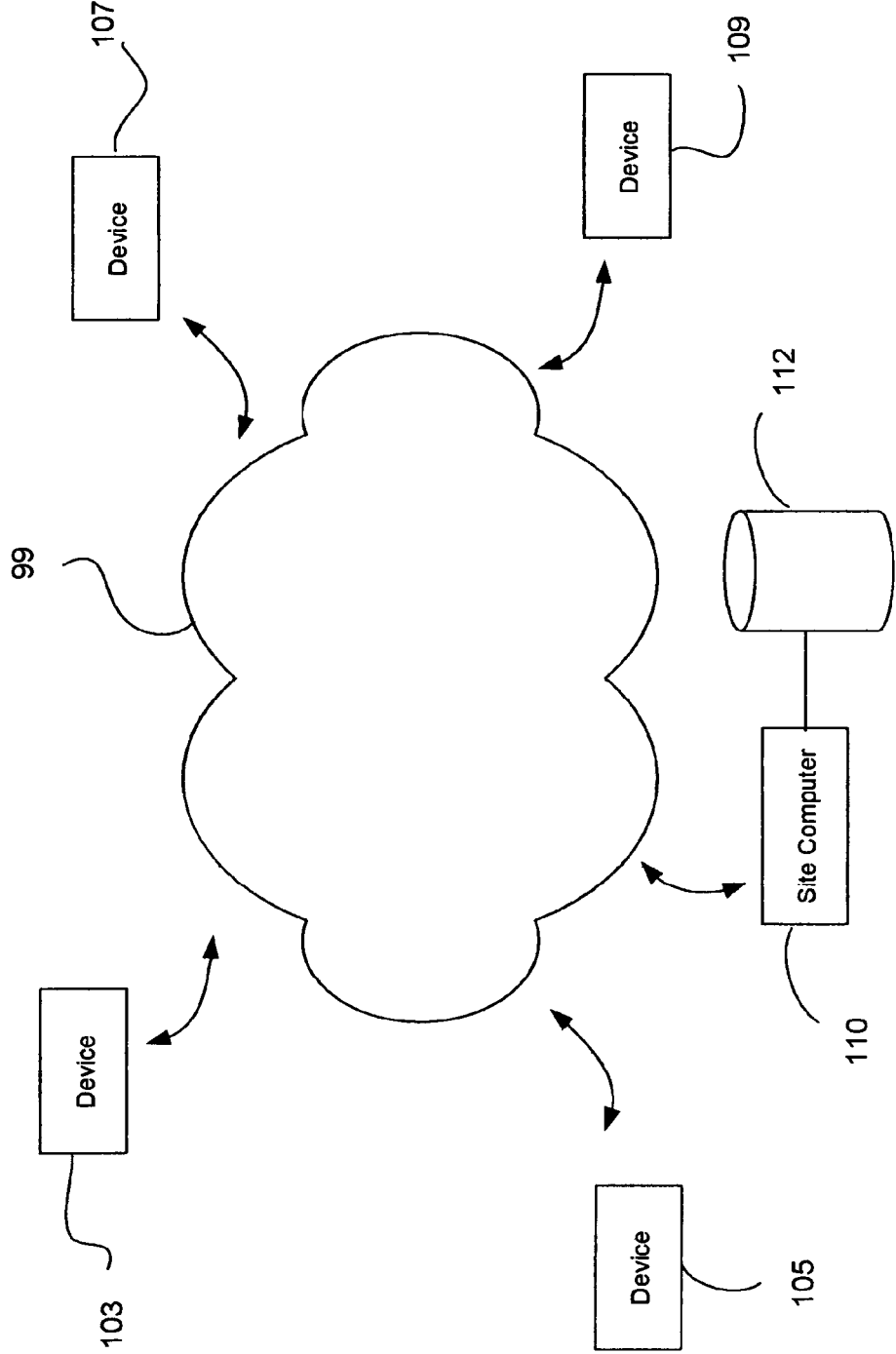
FIG. 1 shows a network linking communication devices in accordance with one of many embodiments of the present invention.
Figure 2:
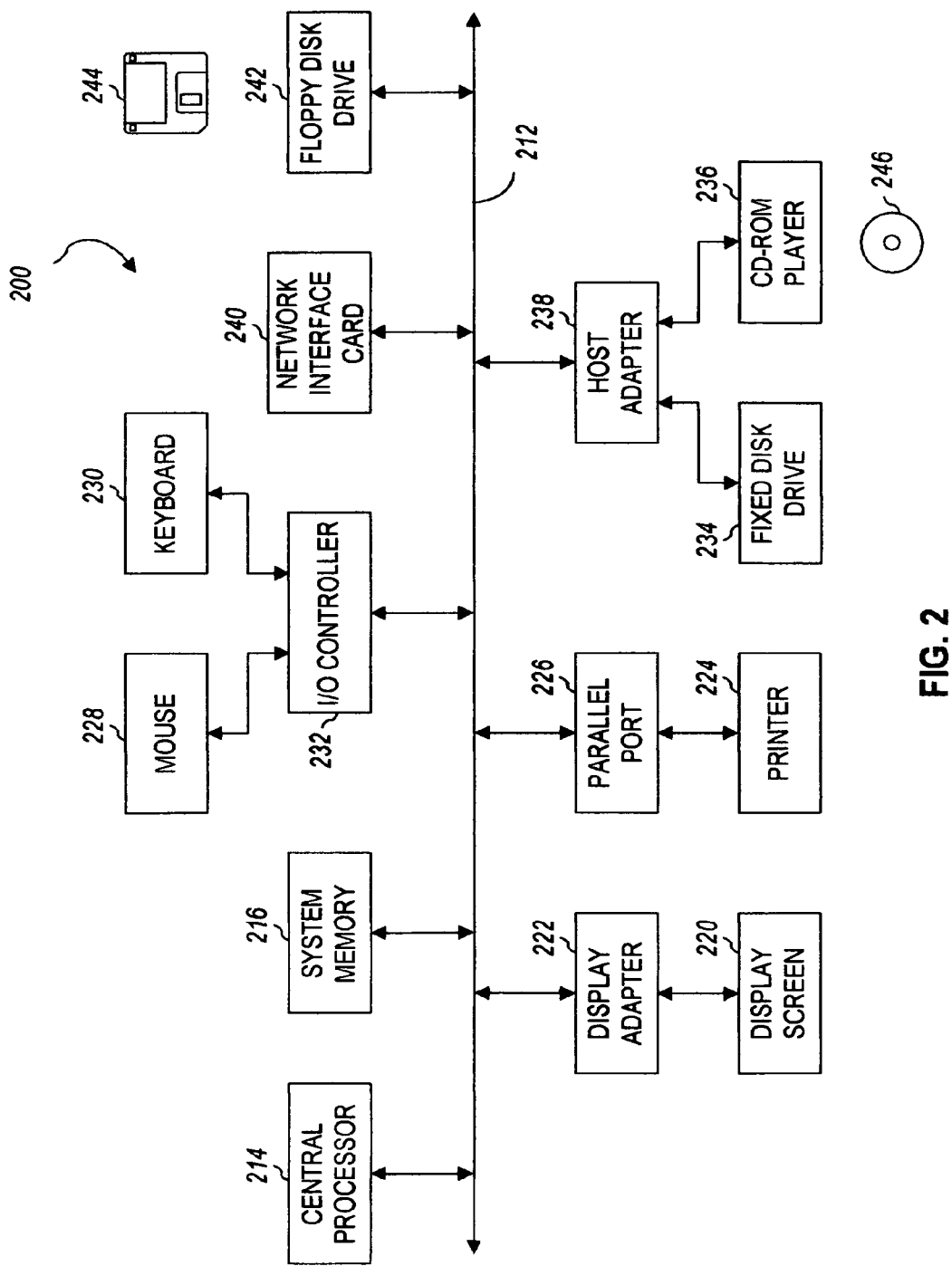
FIG. 2 shows a computer as an example of a communication device in accordance with one of many embodiments of the present invention.

FIG. 1 illustrates electronic communication devices 103, 105, 107, and 109 linked over a network 99 to create, transmit, and receive electronic messages, as well as provide data to and receive data from a local or remote database. Any one of the communication devices 101, 103, 105, and 109 may be a computer, Internet appliance, personal digital assistant (PDA), cellular or mobile phone, set top box, and the like, and any other devices that can receive and transmit information, or provide the capability to access, provide, receive, and modify information to and from a database over wired or wireless networks (hereinafter "devices"). FIG. 2 illustrates a computer as one of many possible exemplary electronic devices shown in FIG. 1. For ease of discussion and illustration, and to reduce unnecessary redundancy, only computers will exemplarily discussed in connection with the present invention as the electronic devices 103, 105, 107 and 109. However, it should be manifestly clear that the present invention applies equally to other devices capable of sending and receiving information in electronic and other formats facilitating remote communications, although their operation may not be explicitly discussed. The network 99 could be any kind of communications network. The network could be a local area network or a wide area network and could be a private or public network of any size or scope. In one embodiment of the present invention, the network 99 is the Internet. The computers, as examples of communication devices 103, 105, 107, and 109 may be linked to computer modems to support communications using protocols such as TCP/IP (Transmission Control Protocol/Internet Protocol) or SLIP/PPP (Serial Link IP/Point-to-Point Protocol). As will be appreciated by those of ordinary skill in the art, other interactive communications media are possible as well. For example, the network 99 can include interactive television networks, telephone networks, wireless data transmission systems, two-way cable systems, customized computer networks, interactive kiosk networks, automatic teller machine networks, and the like, or combinations thereof.

FIG. 2 illustrates basic subsystems of a computer system 10 suitable to implement the communication devices 103, 105, 107, 109 illustrated in FIG. 1. The computer system 200 includes a bus 212 that interconnects major subsystems such as a central processor 214, a system memory 216, and external devices such as a display screen 220 via a display adapter 222, a printer 224 via a parallel port 226, a mouse 228 and a keyboard 230 via an input/output (I/O) controller 232, a fixed disk drive 234, and a CD-ROM player 236 via a host adapter 238, a network interface card 240, and a floppy disk drive 242 operative to receive a floppy disk 244.

Many other devices or subsystems (not shown) can be connected, such as a scanning device, a touch screen, and others. Also, it is not necessary for all of the devices show in FIG. 2 to be present to practice the present invention. Furthermore, the devices and subsystems may be interconnected in different ways from that shown in FIG. 2. The operation of a computer system such as that shown in FIG. 2 is readily known in the art and is not discussed in detail here. Source code to implement some embodiments of the present invention, as discussed in more detail below, may be operatively disposed in system memory 216 or stored on storage media such as fixed disk drive 234, floppy disk 244, or a CD-ROM 246 that is operative with the CD-ROM player 236.

Figure 1A:
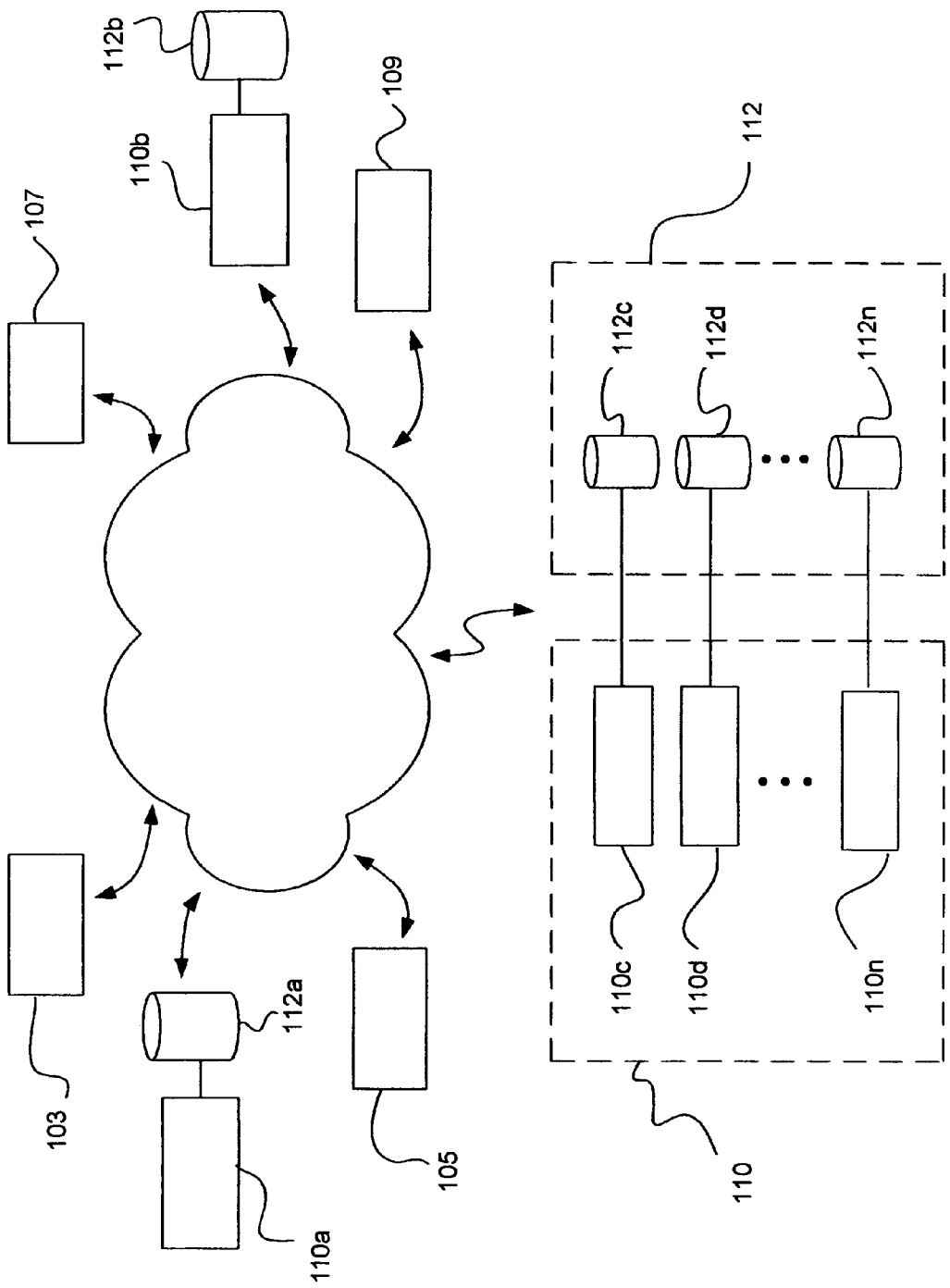
FIG. 1A shows a network linking communication devices in accordance with another of many embodiments of the present invention.

In accordance with the present invention, as exemplarily discussed in connection with the home health care industry, the functionality of the present invention allows for various kinds of manipulation and handling of health records of a patient. The health records can be created, stored, maintained, modified, accessed, organized, shared, transmitted, disassembled, deconstructed into component parts or fields, categorized, or otherwise controlled or manipulated or handled in connection with a site computer 110, which is also included as part of the network 99 of FIG. 1. The site computer 110 has a Universal Resource Locator (URL). The site computer 110 includes an electronic database 112. The database 112 stores, collects, organizes, retrieves, transmits, and manipulates information relating to the health records of patients, as discussed in more detail below. In one embodiment, the site computer 110 including the database 112 are implemented by a server including a database. In other embodiments of the present invention, a plurality of servers in a distributed network, rather than just one, substitute for the site computer 110. In that embodiment, each server can be associated with a particular geographical area. For example, as shown in FIG. 1A, if two servers/databases are implemented in accordance with the present invention, one server/database 110a/112a can handle the health records of patients residing in the western portion of the area over which the present invention is implemented while another server/database 110b/112b can handle the health records of patients residing in the eastern portion of the area. Of course, any number of servers and/or databases can be implemented. In accordance with another embodiment of the invention, depending on the size of the database and other factors, many servers/databases 110c . . . 110n/112c . . . 112n can be employed or dedicated to perform a given task or function or store given information, rather than or in addition to being dedicated to a geographical area, in accordance with the present invention as discussed in more detail below. The site computer 110 and the database 112 are discussed below as separate items. Of course, it will be appreciated that the discussion below includes embodiments of the present invention that integrate the server and the database into a single unit capable of performing the function of separate servers and databases.

The site computer 110 can be accessed to create, store, and provide other functionality regarding a health record of a patient. To create a health record, a health care professional (hereinafter "professional") accesses the site computer 110 by, for example, entering the appropriate URL of the site computer 110 into a web browser run by the device 103, 105, 107, 109. For ease of discussion, the devices 103, 105, 107, 109 will be referred to as simply device 103. It will be appreciated that the discussion below of the device 103 applies equally to devices 105, 107, 109. The device 103 is any device selected by the professional that can allow the provision, receipt, and modification of information created and maintained by the site computer 110. In one embodiment of the present invention, the device 103 could be a device that is in physical proximity to the patient. In this way, the professional need not travel far or expend undue time after providing care to the patient before providing health information about the patient to the site computer 110. Because the device 103 is communicatively linked with the site computer 110, the professional can conveniently, remotely, and immediately provide critical health and status information regarding the condition of the patient. The health care professional could be any person or entity authorized or qualified to create a health record of the patient. A health care professional could include a physician, nurse, physician's assistant, nurse's aide, etc.

In addition to professionals, other persons can have access to health records in accordance with the present invention. For example, access is provided to the patient about whom the records are prepared. Furthermore, persons designated by the patient to have access to the patient's health records can have such access. Such designated persons could include, for example, family members or friends of the patient, or other health care professionals who are not necessarily directly or exclusively providing care to the patient, yet still are interested in the condition of the patient. Such designated persons can access the records of the site computer 110 and the database 112 as a way to track, evaluate, or supervise the provision of care for a patient as well as the progress of the patient's welfare.

Figure 3:
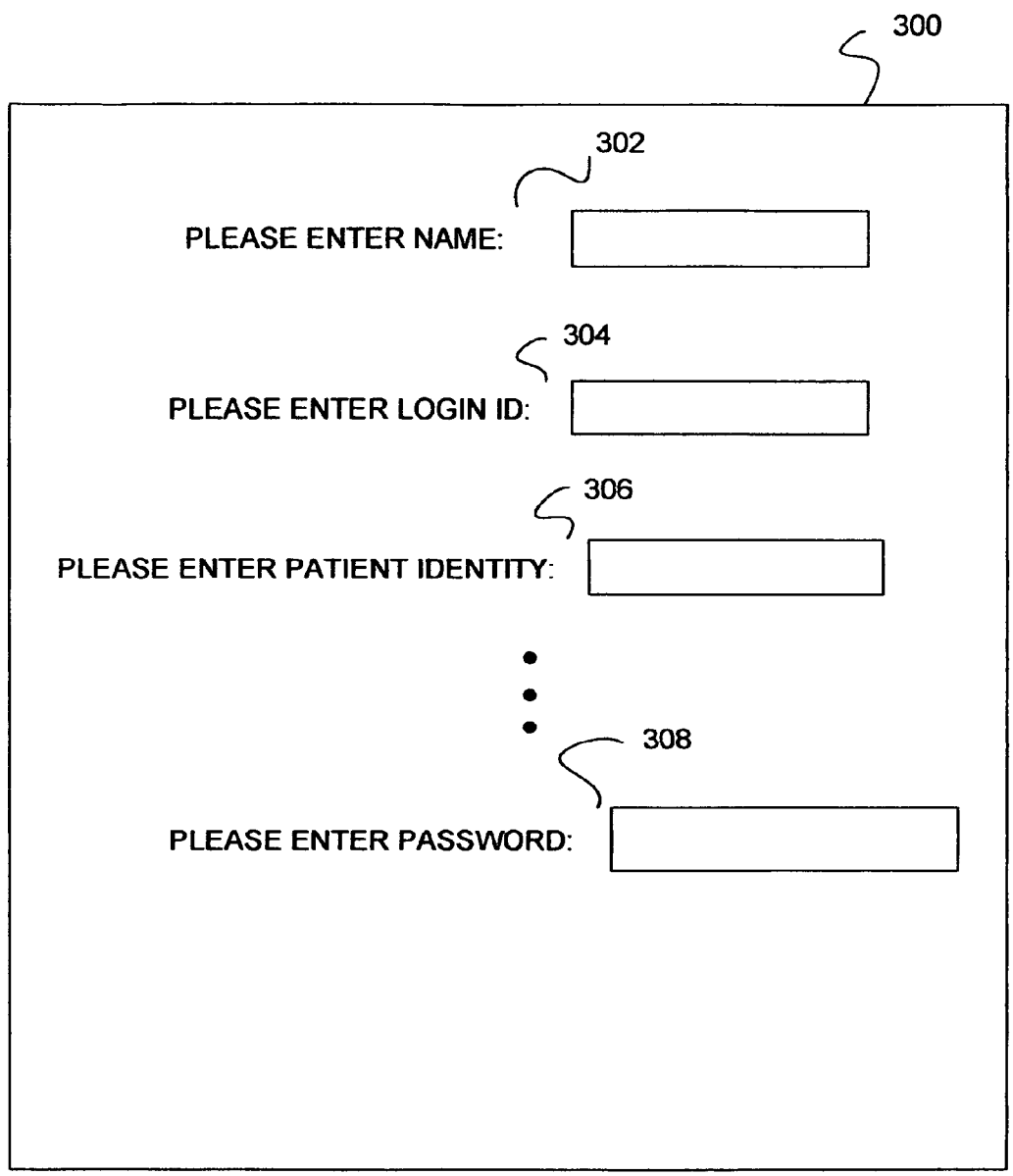
FIG. 3 shows a login ID web page in accordance with one of many embodiments of the present invention.

Upon access to the site computer 110, the site computer 110 provides a login ID web page 300 to the device 103 running a web browser application as shown in FIG. 3. The login ID web page 300 is a security measure to allow only authorized persons to access the site computer 110. The login ID web page 300 includes a name field 302, a login ID field 304, and a patient identity field 306, which prompt the professional or other individual to enter in the associated field, the name of the individual, the individual's login ID, and the name of the patient whose records are to be created or accessed, respectively. The information provided by the individual is then transmitted to the site computer 110 in a conventional manner, for example, a mouse click. Upon receipt of this information, the site computer 110 checks the name and login ID of the individual against the database 112 to ensure that the individual is allowed to have access to the database. This checking by the database 112 may be performed in connection with a special database and/or server dedicated to the checking of login IDs, i.e., a login ID server and a login ID database. The database 112 includes the names and login IDs of all persons who are entitled to create or access health records of the site computer 110. Furthermore, using the patient identity information provided by the individual, the site computer 110 checks to see that, even if the individual is permitted to enter the site computer 110 and access the database 112, the individual is entitled to create or access the health records of the particular patient identified. In another embodiment of the present invention, a password field 308 can be included in the login ID web page 300 to prompt entry of a password by the individual. The password, which could be chosen by the individual, the site computer 110, or the patient, secures access to the records. For example, the patient could obtain a password to allow access to the patient's records. The patient can provide the password to other individuals to allow access the patient's records. Of course, the login ID web page 300 could include additional fields of information required to access the records besides those explicitly described herein. In another embodiment of the present invention, the login ID web page 300 contains other information fields that allow the site computer 110 to identify the person seeking access and determine if access is allowed.

Figure 4:
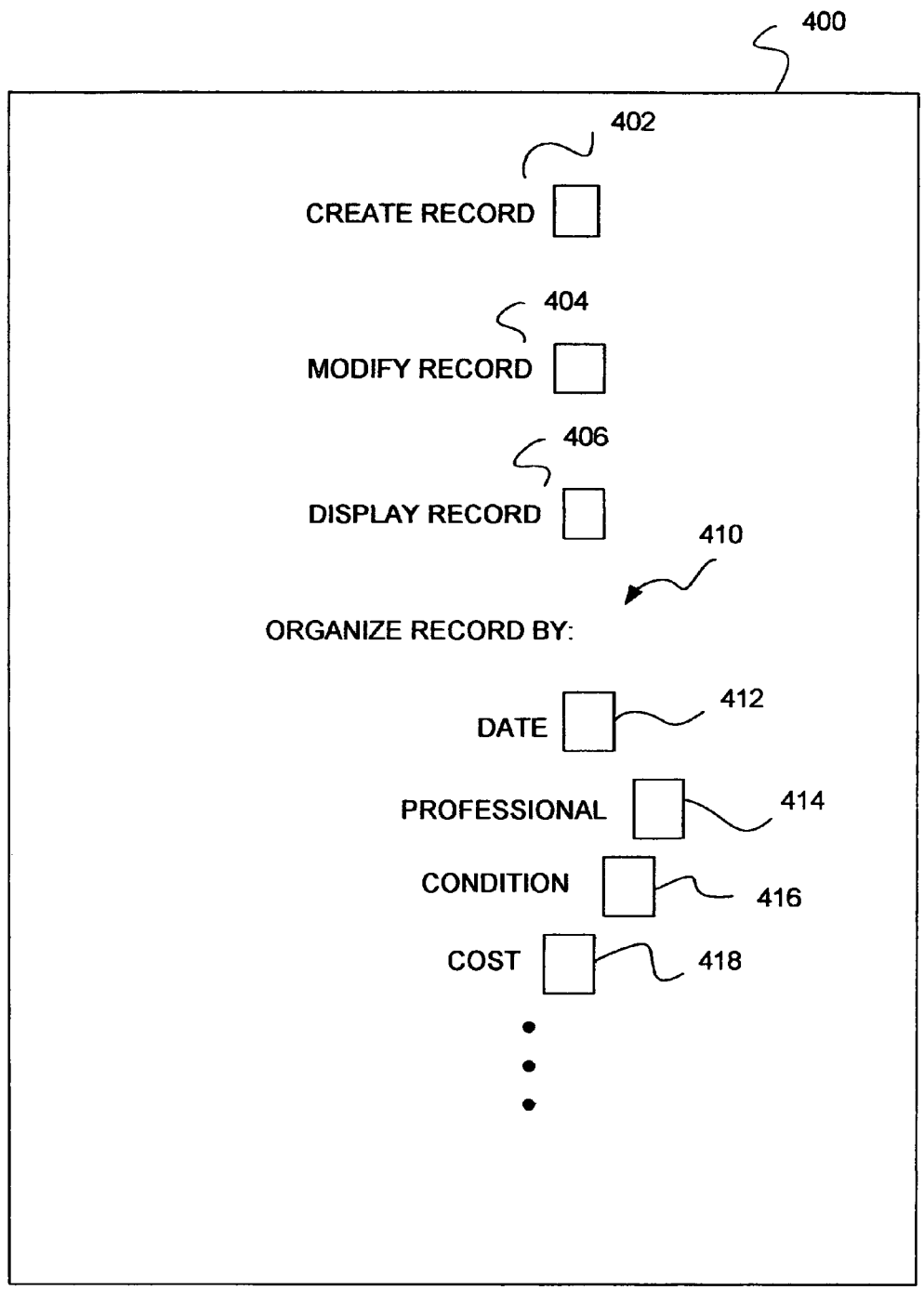
FIG. 4 shows a menu page in accordance with one of many embodiments of the present invention.

If the individual is properly identified by the site computer 110 as one authorized to create or access a health record for the patient, a menu page 400 is provided by the site computer to the device 103 as shown in FIG. 4. The menu page 400 includes a create field 402, a modify field 404, a display field 406, and an organize field 410 which allow the individual to, respectively, create, modify, display, or organize health records. Selection of any of these actions is accomplished in a conventional manner by, for example, a mouse click corresponding to field of the desired action, and transmission of the desired action to the site computer 110. Based upon the login ID of the authorized individual, the site computer 110 allows the individual to perform select actions and tasks. In one embodiment of the present invention, if the login ID provided by the individual identifies the individual as a professional in charge of or supervising or providing care for the patient, the site computer 110 allows the professional to create, modify, display, and organize the records of the patient. If the login ID provided by the individual identifies the individual as not being a professional, but rather the patient, a family member, or friend, for example, then the site computer 110 allows the individual only to display or organize records, not to create or modify them since the individual is not qualified or authorized to do so.

When the professional selects to create a record, the site computer 110 returns a record page 500 which prompts the professional to enter appropriate information about the condition of the patient as well as other kinds of information as shown in FIG. 5. A patient identity field 502, ID number field 504, date of visit field 506, treatment field 508, condition field 510, observations field 512, cost field 514, professional preparer field 516, and access code number field 518 prompt the professional to enter information. As their names imply, the patient identity field 502 prompts entry of the name of the patient for whom the health record is being created; the ID number field 504 prompts entry of an ID assigned to the particular patient; the date of visit field 506 prompts entry of the date and/or time the professional visited the patient; the treatment field 508 prompts entry of information regarding the treatment being provided to the patient; the condition field 510 prompts entry of information regarding the condition of the patient; the observations field 512 prompts entry of information relating to the health or medical observation of the professional in relation to the welfare of the patient; the cost field 514 prompts entry of the charge for the visit by the professional and services rendered or products delivered and whether the charge has or has not been paid; the preparer field 516 prompts entry of the identity of the professional who is creating the record; and the access code number field 518 prompts entry of the access code number of the preparer. The preparer can enter this prompted information using any input method associated with the device 103.

Although the embodiment illustrated in FIG. 5 explicitly sets forth certain kinds of predetermined information included in a health record, it will be appreciated to those of ordinary skill in the art that additional kinds of information could also be included in the health record in accordance with the present invention. Similarly, certain kinds of information could be excluded in such a health record. It will be appreciated by those of ordinary skill in the art that the health record in accordance with the present invention includes any and all kinds of information that would be usefully or desirably documented and recorded to describe a patient's condition, treatment, amounts owed/paid for services rendered, or other information directly or indirectly related to condition and treatment. Once the record is prepared and entered by the preparer, the record is transmitted to the site computer 110 and stored in the database 112 for storage and safekeeping in accordance with conventional database application techniques. In an alternative embodiment of the present invention, the record can be sent to and stored in a special server and/or database dedicated to storing health records for patients.

It will be appreciated that the present invention provides many advantages over the prior art. For example, with respect to the home health care industry in particular, the present invention allows for the immediate creation, modification, or other kind of handling of a patient's health care records. The professional who provides care and assesses the condition of the patient can prepare health care records in the home of the patient using the device 103 in the home, or in a location adjacent to wherever the patient may be. By doing so, a contemporaneous record of the patient's condition can be made and thus no time is wasted in potentially sharing the record to other entities interested in the patient, as is discussed in more detail below. Furthermore, a complete and accurate record can be made while the assessment or opinion of the professional is still fresh in his or her mind. This way, interested entities can timely supervise the rendering of care for the patient and stay abreast of the patient's welfare. In addition, on-the-fly access by the professional to the patient's records permits review of the patient's history and thus better subsequent assessment of and treatment for the patient.

As shown in FIG. 4, the menu page 400 includes the modify record field 404 and the display record field 406. Selection by a professional or other person who is authorized to access a particular record of the display record field 406 causes a predetermined or desired record to be retrieved from the database 112, or other storage device or area, and displayed on the device 103 used by the professional or other person. Display of a particular one or group of records can be accomplished in a conventional manner by allowing the individual to identify the records desired. For example, the site computer 110 can provide a web page (not shown) that allows a the individual to identify a record by these criteria: name of patient, name of professional caring for patient, date of visit by professional, or any other information, including the information provided in the fields of the record 500. Display of the record allows access and review of the record and thus assessment or analysis of the patient's condition and treatment in connection with the displayed record. Display of a patient's records in accordance with the present invention provides significant advantages over the prior art in the oversight and care of the patient. Rather, than waiting to see documentary records that are conventionally stored in a single location only, all interested persons in the patient's condition who have access to the records are, in accordance with the present invention, able to quickly, timely, remotely, and conveniently review the patient's condition and welfare. Because this ability allows for increased oversight of the patient's condition, the quality of the patient's care is greatly enhanced.

Selection of the modify record field 404 causes a predetermined or desired record to be retrieved from the database 112, or other storage device or area, and initially displayed on the device 103 used by the professional or other person. Display of the record allows access and review of the record and thus assessment or analysis of the patient's condition and treatment in connection with the displayed record. After display of the record, using input techniques of the device 103, the professional or other person is then free to modify the contents of the retrieved record as desired and as appropriate. For example, if information prompted by any of the fields of the record 500 is to be modified, then the information of the record can be changed as desired by the professional or other person. The record can be modified in any one of various ways. For example, assume that the cost field 514 initially indicates that a charge for service has not been paid. Assume further that later the payment is made. Accounting or other personnel for the health care provider providing care for the patient can modify the information provided in the cost field 514 to indicate that payment has been made. After modification of the record is complete, the record is again transmitted to the site computer 110 and the database 112 in a conventional manner as described in part above.

Figure 6:
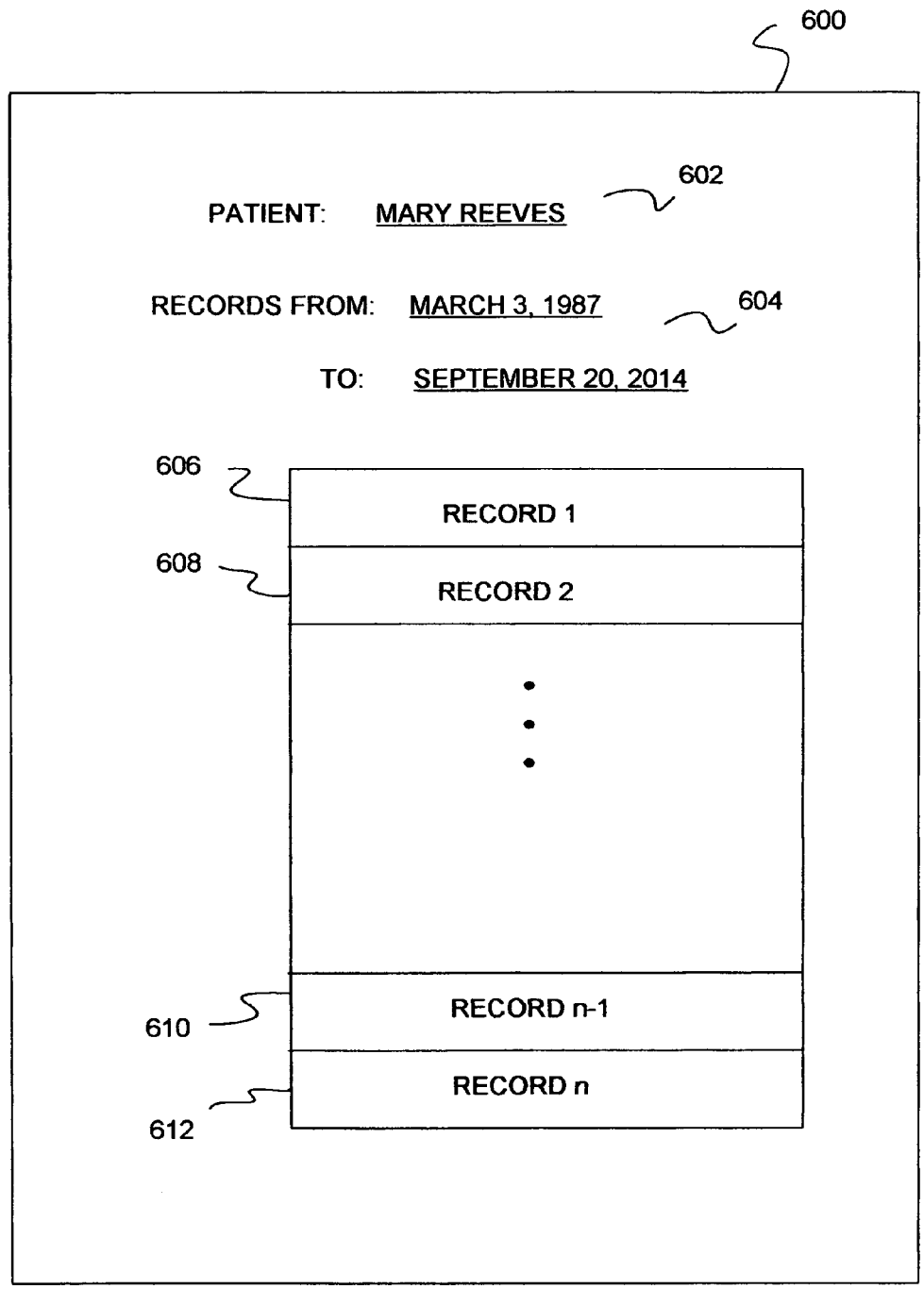
FIG. 6 shows a file history in accordance with one of many embodiments of the present invention.

The menu page 400 also includes the organize record field 410, which in turn includes a date field 412, a professional field 414, a condition field 416, and a cost field 418. Selection of the organize record field 410 allows a desired compilation or organization of records based upon various factors such as date of visit, identity of professional, condition of patient, and charge for care, or any other factor or combination of these or other factors. Once such a selection is made and provided to the site computer 110, the site computer 110 and/or the database 112 receives, stores, and organizes the records of patients, like the record 500 discussed above. In one embodiment of the present invention, the database 112 collects and arranges all of the records of a patient in a file history 600 as shown in FIG. 6. The file history 600 of a patient illustrated in FIG. 6 is a simplified logical depiction and arrangement of various records associated with a patient. The file history 600 includes a patient field 602 which identifies the patient associated with the file history 600. The file history 600 also includes a time field 604 which provides the chronological span of the records constituting the file history 600. The file history 600 includes n number of records: record 1 606, record 2 608, . . . , record n−1 610, and record n 612. In the illustrated and one of many possible embodiments of the present invention, the records are arranged in chronological order based upon the date field 412, and the information provided in the date of visit field 506 of various records.

Of course, many other techniques to arrange the records are possible. As only one of many examples, the records could be extracted and/or arranged by grouping the records according to any of the component parts, i.e., fields, identified in the record 500, in addition to the specific fields identified in the organize record field 410 of the menu page 400. It will be appreciated to those of ordinary skill in the art that the various fields of a particular record in the database 112 can be separately and logically organized among the other fields of that record as well as fields from all other records in the database 112 in one of a variety of conventional techniques using conventional database application software. The file history 600 need not be compilations of entire records. Rather, in another embodiment of the present invention, the file history 600 can be a compilation of only one, or many, selected field(s) of various records. Thus, selection of the organize record field 410 can allow for the creation of various file histories according to myriad factors and desired fields. In one embodiment of the present invention, file histories, once compiled, are stored in the site computer 110 and the database 112 for later access. In one embodiment of the present invention a dedicated server and database are used to store and allow access to compiled files histories.

As another example, in accordance with the present invention, selection of the organize record field 410, and in particular the cost field 418, for a particular patient causes all of charge information corresponding to the cost field 514, and no other fields, of the records of the patient to be compiled in a file history. In this case, such a file history relating only to the charges for care can be provided to the patient, or the accounting department of the health care agency of the professional providing care to the patient. In allowing this simple yet innovative and powerful way to organize data, the patient can expeditiously discover financial information relating to the care of the patient. Accordingly, the patient can quickly determine the cost of treatment and monies owed to the health care provider, if any. The ease of organizing cost information for a particular patient is invaluable to a health care agency as well. It will be appreciated that one significant shortcoming of conventional accounting practices of health care providers is in the delay between the time that care is rendered and the time that the patient can be billed for the care. Such delay entails considerable expense and significant administrative effort. One cause of such delay is because the professionals often must travel away from their health care agencies to see patients. Another cause is that professionals often work in the field and, as part of their jobs, are not routinely present at their agencies, i.e., they often do not have to go into work. As a result, contact between the professionals and their agencies is sometimes infrequent.

Conventional techniques involve waiting for the professional to provide the accounting department, or billing personnel, of the health care provider the necessary billing information to invoice the patient, which can require undue time and effort and, thus, significant expense. In contrast, the method and system of the present invention allows the health care provider to not require direct, personal contact between the professional and the accounting department of the health care provider before the bill to the patient is sent out. The accounting department can simply selectively access the records of the patient by the device 103 and organize them according to the cost field 514 to obtain any necessary information. In fact, in accordance with another embodiment of the present invention, the accounting department of a health care agency can prompt the professional to provide in the record 500 all information necessary for the preparation of the bill to the patient. Because the professional can and likely will enter the record of the patient regularly and soon after a patient visit, the compilation of cost information from records is an effective way to facilitate preparation of bills and invoices and, accordingly, significantly improve the cash flow of health care agencies. The present invention's obviation of direct or regular contact between professional and agency is useful for many reasons and in many situations including, for example, when the professional is often traveling or in the field or otherwise not predisposed to having frequent contact and communication with the professional's agency.

Figure 7:
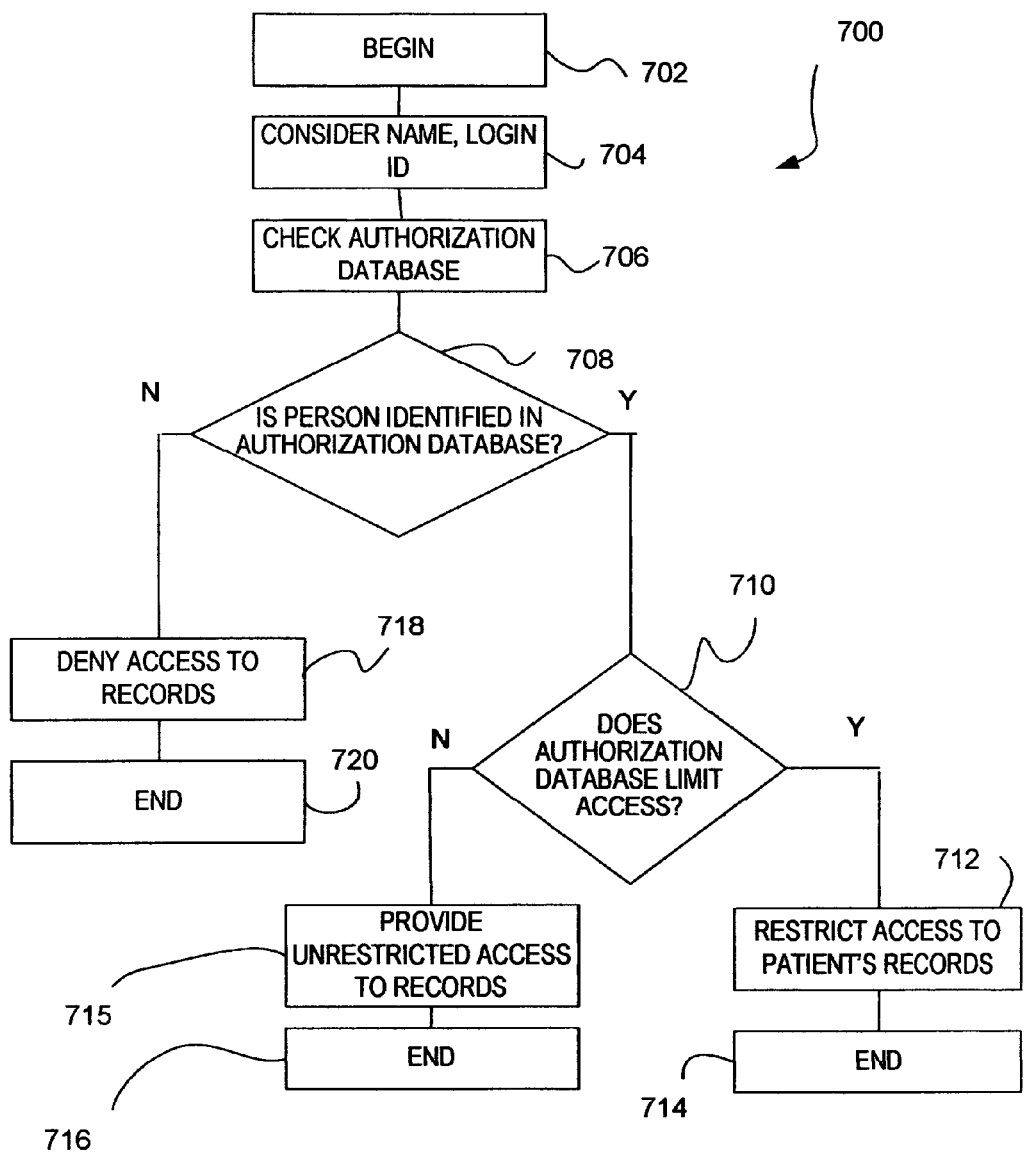
FIG. 7 shows a flow diagram of record access provision in accordance with one of many embodiments of the present invention.

To ensure the privacy of the patient and limited access to the records of the patient, in one embodiment of the present invention, persons seeking records are allowed only to access and organize the selective portions of a patient's records, as shown in flow logic 700 of FIG. 7. At a step 702, the logic begins. The logic proceeds to a step 704 where the site computer 110 considers the provided login ID and name of the person seeking records access. Of course, other kinds of identification information could be provided to the site computer. The logic proceeds to a step 706 where the identity of the person is compared against one or more authorization databases. Each authorization database is programmable and lists names of persons entitled to access portions or entireties of the patient's records and also identifies which portions of the records are accessible by the person. Such comparison can be implemented by a recognition function under conventional techniques of the site computer 110 and the database 112, or as mentioned above, servers and/or databases dedicated to the task of determining which records of patient a person is allowed to access. The logic proceeds to a decision step 708 where the logic determines if the person is identified in an authorization database. If the result of decision step 708 is affirmative, the logic 700 proceeds to decision step 710 where the logic determines if the authorization database requires the person to have limited access to the records of the patient. If the result of decision step 710 is affirmative, the logic proceeds to a step 712 where the person is restricted in accordance with the authorization database to only portions of the patient's records. Other portions of the records are not accessible by that person. The logic proceeds to a step 714 where the logic ends. If the result of the decision step 710 is negative, the logic proceeds to a step 715 where the person has unrestricted access to the records and the logic proceeds to step 716 where the logic ends. If the result of decision step 708 is negative, the person is not authorized to have any access to records, and the logic proceeds to a step 718 where the logic prevents the person from accessing the records. The logic proceeds from the step 718 to step 720 where the logic ends.

For example, in accordance with one embodiment of the flow logic 700 of the present invention, an authorization database is provided and/or programmed for storing information regarding accounting personnel who are allowed only to access the financial records or component portions of records relating to financial information of a patient. Such an authorization database includes the name and login ID of all accounting personnel who are entitled to access such records, or portions or fields thereof relating to financial information, for a particular patient. In addition, the authorization database restricts access by the listed accounting personnel to any information in the records beyond the financial information. Thus, the site computer and the database determine whether the person seeking access is entitled to any access and, if so, to what extent. If the person is accounting personnel, then the site computer and database allow the person only to access the financial records of the patient. Thus, only cost information associated with the cost field 514, or other information associated with other fields relating to financial topics, of a record can be accessed.

As another example, in accordance with another embodiment of the flow logic 700 of the present invention, an authorization database is provided for storing information regarding friends and family selected by a patient to have access to the patient's records. Assume that the patient suffers from two conditions. The patient may choose to allow one group of persons to have access to records relating to care and treatment for one condition only. Likewise, the patient may choose to allow another group of persons to have access to records relating to care and treatment for the other condition only. Thus, the authorization database can be programmed to allow selective access to the patient's records depending on the person seeking access and depending on the condition discussed for particular records. In this regard, the authorization database could be programmed to separately store and identify all the persons allowed to access records pertaining to the care and treatment of one condition and separately identify all the person allowed to access records pertaining to the care and treatment of another condition. Furthermore, all of the records of the patient can be organized according to the information provided in the condition field 510 to associate each record with a given condition. Such organization can then be reflected in the authorization database to accomplish the patient's desire to allow selective access based upon the parameters of persons seeking access and particular condition of the patient.

Other embodiments are possible. The flow logic 700 could be implemented to allow access to a patient's record only if the record did not relate to a predetermined condition of the patient. The flow logic 700 could be alternatively implemented to allow access only to records documenting costs less then or more than or in a range between predetermined amounts. As another example, the flow logic 700 can be implemented to deny access to all records indicating that the condition of the patient is poor while allowing access to all other records of the patient. It will be appreciated by those of ordinary skill in the art that the authorization database as implemented by the site computer and database can be programmed to allow partial or selective access to a patient's records based on many predetermined parameters, including the information provided in the fields 502-518, in addition to the examples described above.

Figure 8:
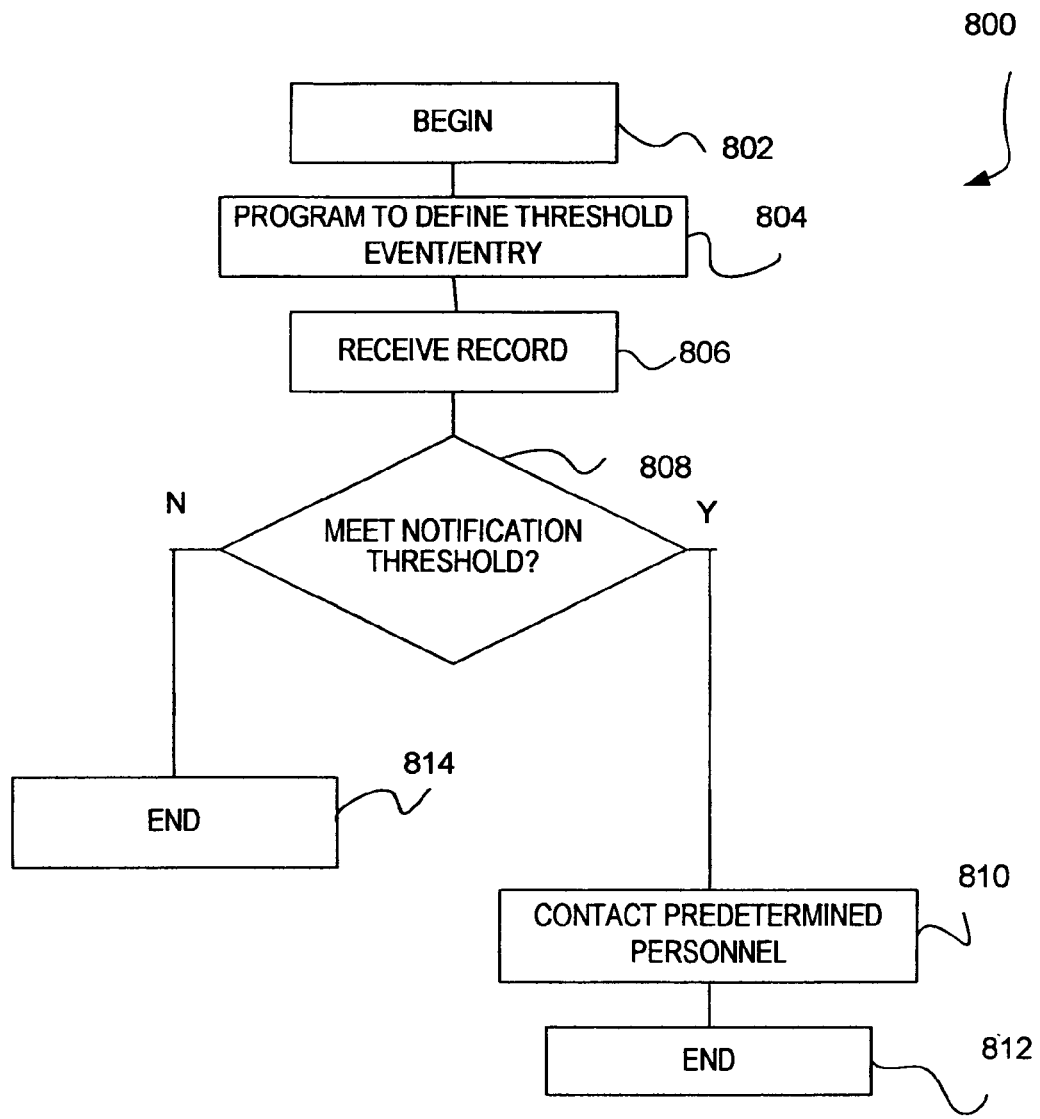
FIG. 8 shows a flow diagram of notification upon threshold satisfaction in accordance with one of many embodiments of the present invention.

FIG. 8 illustrates flow logic 800 for automatically providing alerts based upon a patient's records. The logic begins at a step 802 and proceeds to a block 804 where the site computer 110 is programmed to identify a threshold or predetermined event as documented in a record and respond upon such identification. The logic proceeds to a step 806 where the record is received by the site computer 110. The logic proceeds to a decision step 808 where the record is analyzed and the logic determines if the threshold event has occurred. If the result of the decision step 808 is affirmative, the logic proceeds to a step 810 where a predetermined action is taken. In one embodiment of the present invention, the predetermined action includes contacting certain individuals, entities, or institutions that may be interested in knowing about the occurrence of the threshold event. The logic proceeds from step 810 to a step 812 where the logic ends. If the result of the decision step 808 is negative, the logic proceeds to a step 814 where the logic ends.

The flow logic 800 can be implemented for various purposes and applications. In one embodiment of the present invention, the flow logic 800 is implemented by and in the site computer 110 and/or the database 112 to provide an emergency notification about the condition of a particular patient to various interested individuals. For example, the site computer 110 or database 112 can be programmed initially to look for any entries in records for a particular patient that relate to a given threshold event. Further, the database 112 can be programmed to include information about which persons should be notified upon occurrence of the threshold event, including the identity and contact information for each person. Assume that the site computer 110 is programmed to look for any records that relate the condition of the patient as being critical or worse. The site computer 110 can be programmed to specifically find this kind of information in a record in the condition field 510. In one embodiment of the present invention, the information provided in the condition field 510 includes keywords, such as "stable", "poor", "critical", "terminal", etc., that can be readily recognizable by the site computer 110 through conventional programming techniques. Of course, other ways for the site computer to determine the condition of the patient are possible. For example, the individual who created the record can be prompted by the site computer 110 through the record page 500 to enter a number from a numerical range corresponding to the condition of the patient with, for example, "1" corresponding to excellent health and "10" corresponding to terminally ill. The site computer can interpret these numbers to assess the condition of the patient. The site computer 110 is programmed initially to look for all records indicating that the condition of the patient is poor, for example, corresponding to a numerical range associated with a poor condition (e.g., between "7" and "10") or, for example, corresponding to keywords such as "poor", "critical", etc.

Upon detection of records indicating that the threshold event has occurred, the site computer 110 determines from its appropriately programmed database which persons should be contacted. These persons could include medical health professionals who may desire to treat the patient or provide specialized care, family members of the patient, or other persons interested in the condition of the patient. The determination causes the site computer 110 to automatically initiate contact with or notify these persons. This notification can occur in various ways. The site computer can transmit a notice to the interested person using any one of many different conventional techniques, including, for example, electronic mail notification. Alternatively, the site computer can transmit a notice to health care personnel or others who then, in turn, contact each interested person personally, telephonically, electronically, or otherwise.

Figure 9:
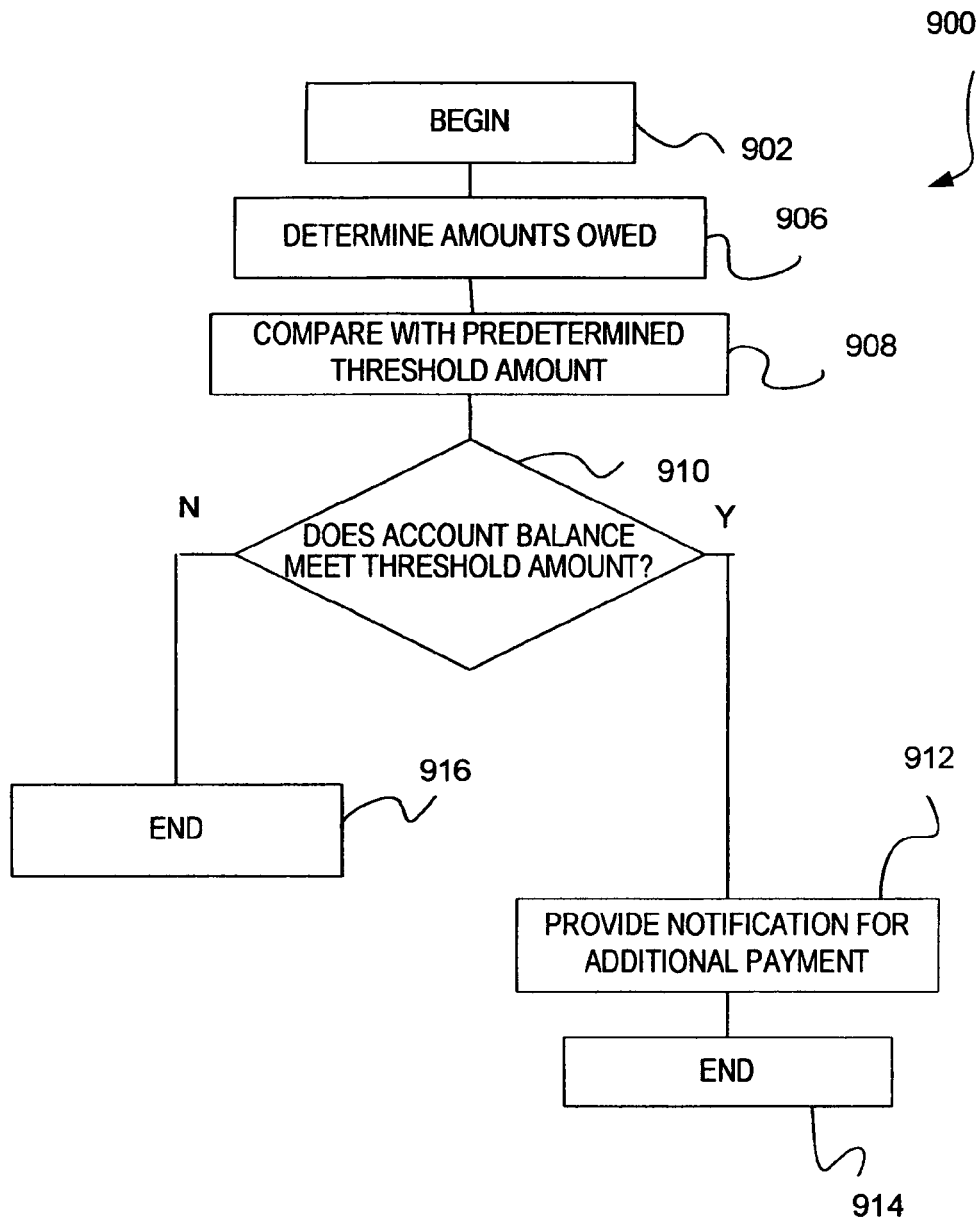
FIG. 9 shows a flow diagram of accounting notification in accordance with one of many embodiments of the present invention.

FIG. 9 illustrates flow logic 900 of a technique in accordance with the present invention to notify accounting personnel of a health care provider regarding current balance information for a patient receiving care from the health care provider. The logic begins at a step 902 and proceeds to a step 906 where the site computer collects account balance information for a particular patient by collecting the information provided in the cost field 514 of the patient's records. The logic proceeds to a step 908 where the account balance is compared with a predetermined threshold amount. The logic proceeds to a decision step 910 to determine if the account balance has met the predetermined threshold amount. If the result of decision step 910 is affirmative, the logic proceeds to a step 912 where the patient is automatically notified to make additional payments. The notification can be made using any one of many conventional techniques as discussed above. The logic proceeds from step 912 to step 914 where the logic ends. If the result of decision step 910 is negative, the logic proceeds to a step 916 where the logic ends.

The flow logic 900 can be implemented for various purposes in accordance with the present invention. For example, in one embodiment of the present invention, the accounting department of a health care provider uses the flow logic 900 to invoice the patient for additional payments. The accounting department periodically and/or automatically uses the site computer and the database to organize and collect the financial information relating to the care of the patient from the patient's records. If the amount of money owed to the health care agency, the account balance of the patient, exceeds a threshold amount, the accounting department may choose to notify the patient to provide additional payments using any one of many conventional notification techniques discussed above. Alternatively, the flow logic 900 can be used to selectively invoice the patient for services rendered. For example, assume a health care provider chooses not to invoice patients until a certain account balance is attained. This choice may be made as a matter of business policy, administrative convenience, or the patient's preference, or other reason. After accumulating financial information from, for example, the cost field 514 of a patient's records, the accounting department of the health care provider can withhold sending the bill until the costs of services rendered reaches the threshold amount. It will be appreciated that the flow logic 900 can be implemented in various other ways in other embodiments apart from those explicitly described herein.

Figure 10:
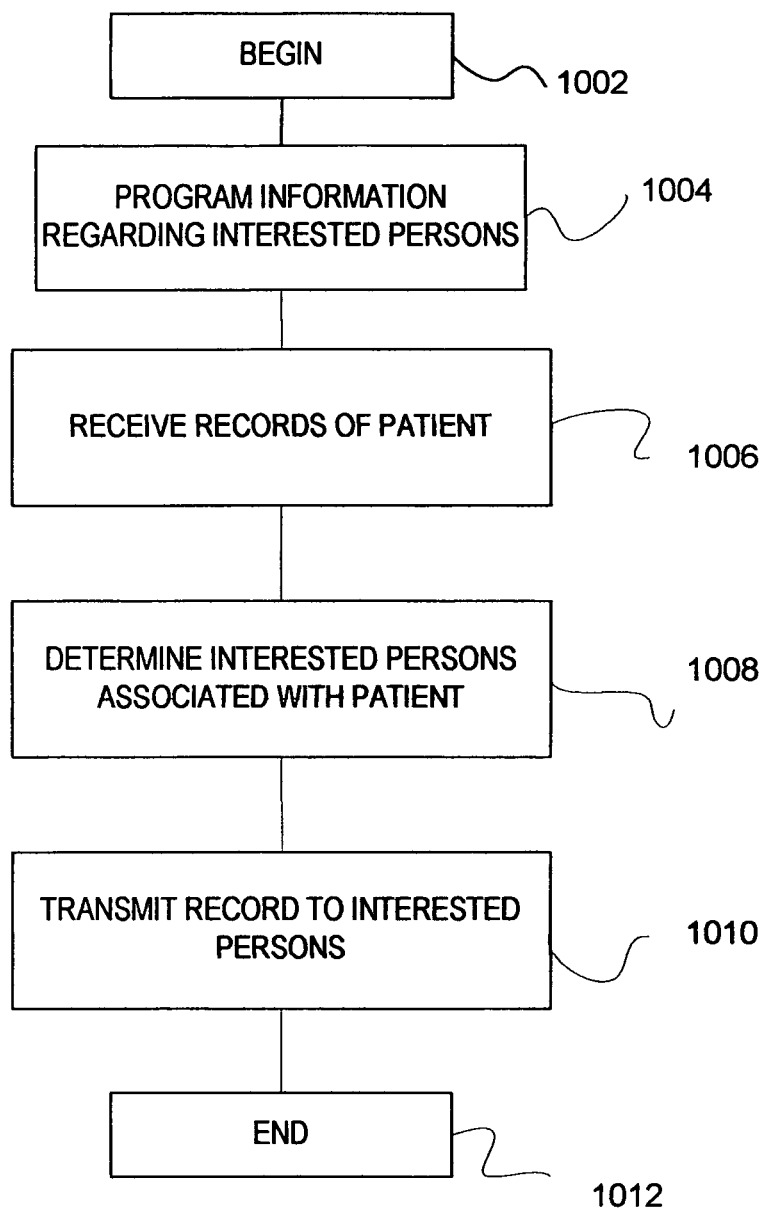
FIG. 10 shows a flow diagram of automatic record provision in accordance with one of many embodiments of the present invention.

FIG. 10 illustrates flow logic 1000 for selectively and automatically providing a patient's records to interested persons. In this way, interested persons can be automatically and routinely apprised of the patient's condition and status. At a step 1002 the logic begins and proceeds to a step 1004 where site computer 110 and database 112 initially receive information relating to the identity of and contact information for persons who are designated to receive records, or portions thereof, of a patient. This information, like other kinds of information provided to the site computer and database, can be programmed in any conventional way. The logic proceeds to a step 1006 where the site computer and database receive records created by professional personnel who care for the patient. The logic proceeds to a step 1008 where, upon receiving each record, the site computer 110 and the database 112 identify the persons, if any, designated to receive the record. The logic proceeds to a step 1010 where the record is transmitted or otherwise communicated to the designated persons. In one embodiment of the present invention, the transmission or communication of the record, or portion thereof, can involve providing the record as an electronic message in the form of an email sent to the address provided as part of the designated person's contact information. Of course, other transmission techniques are possible. For example, the records could be sent using postal mail or by facsimile. The logic proceeds to step 1012 where the logic ends. Instead of sending an actual record or portion thereof to interested persons, in another embodiment of the present invention, during the step 1010 only a notice is sent to interested persons. The notice would indicate the creation of a new record, identify the record, and invite the interested persons to access the site computer 110 to access and review the record.

While the preferred embodiment, and alternative embodiments, have been illustrated and described, it will be appreciated that various changes can be made therein without departing from the spirit and scope of the invention. For example, the web pages illustrated in the Figures are simplified depictions. The Figures discussed above in connection with the present invention include preferred exemplary depictions of web pages in accordance with the present invention. It will be appreciated that web page(s) other than those specifically illustrated can be designed and implemented in accordance with the present invention. The depicted web pages can contain any mixture of text, graphic imagery, pictures, sounds, motion picture information, links, and advertising notwithstanding any basic, exemplary depiction thereof in all of the Figures discussed in connection with the present invention.

It will also be appreciated that, although the present invention preferably includes the use of the Internet, which is often accessed in English, the present invention need not be implemented in English exclusively. Other languages appearing on the web pages could be used depending on many factors including, for example, the linguistic abilities of targeted users, or the language capabilities of the potential users situated in the geographical region over which the present invention is implemented, or both. Of course, the present invention could be implemented using a selective combination of different languages such as Chinese, Hindi, German, Spanish, etc.

FIG. 5 is a record page 500 having fields that prompt a preparer of the record to provide certain information. It will be appreciated that the record page 500 can prompt the preparer to input additional kinds of information other than those specifically set forth herein. Likewise, the record page 500 can be designed not to prompt certain kinds of information discussed above. The record page 500 can be designed to include fields to prompt the provision of desired information for any particular need or purpose based on various factors relating to, for example, medical condition, financial status, location, medical profile, age of patient, and any and all other medically information pertinent to the health and welfare of the patient. In accordance with conventional database software applications, the records page 500, when completed by the preparer and transmitted to the site computer 110 is converted to an electronic record. The electronic record can be stored, modified, organized, deconstructed into component fields, compiled and otherwise manipulated in accordance with conventional capabilities of electronic databases and related technologies.

The present invention contemplates programming the site computer 110 and database 112 with various information. For example, information relating to passwords, persons entitled to access records, threshold events triggering notifications or requests, persons receiving notifications, etc. are programmed. It will be appreciated that the programming of the site computer(s) and the database(s) can be performed locally at the location of the site computer(s) and the database(s) or remotely at, for example, devices 103, 105, 107, 109 that are in communication with the site computer(s) and databases(s). The technique of programming can be performed in any conventional manner.

Furthermore, a portion of the discussion above relates specifically to the home health care industry. It will be appreciated that the present invention applies equally to other health care contexts. For example, the communication device can be used by a health or mental care professional rendering care for a patient at a location apart from the patient's home, for example, a medical clinic, hospital, care facility, or other place where care is offered. In that case, the device 103 can be used at or near the place where the care is rendered to manipulate health care records for the patient in the various ways described above.

Consequently, within the scope of the appended claims, it will be appreciated that the present invention can be practiced otherwise than as specifically described herein.

I claim:

1. A computer implemented method comprising:
   storing, via a computer system, records including types of data concerning a patient;
   receiving, via the computer system, access rules to selectively control electronic access to the types of data, the access rules determined by the patient;
   controlling, via the computer system, access to the types of data by applying the access rules determined by the patient;
   providing, via the computer system, to a first group of individuals access to a first type of data concerning the patient according to the access rules determined by the patient;
   providing, via the computer system, to a second group of individuals access to a second type of data concerning the patient according to the access rules determined by the patient;
   receiving, via the computer system, an indication about a threshold event relating to the patient;
   determining, via the computer system, occurrence of the threshold event by comparing a numerical value indicative of a condition of the patient with a threshold value associated with the threshold event;
   providing, via the computer system, a notification to an entity selected by the patient in response to the occurrence of the threshold event, wherein the selected entity is not the patient, the threshold event and the notification relating to the first type of data; and
   withholding, via the computer system, the notification from the second group of individuals.

2. The method of claim 1 wherein at least a portion of the first type of data is identical to at least a portion of the second type of data.

3. The method of claim 1 wherein the first type of data and the second type of data are stored in at least one database.

4. The method of claim 1 wherein the first type of data includes sensitive information of the patient.

5. The method of claim 1 wherein the first type of data includes medical information of the patient.

6. The method of claim 1 wherein the first type of data includes financial information of the patient.

7. The method of claim 1 wherein the first type of data includes medical information of the patient, and the second type of data includes financial information of the patient.

8. The method of claim 1 wherein the access rules deny the second group of individuals access to the first type of data.

9. The method of claim 1 wherein the access rules are determined exclusively by the patient.

10. The method of claim 1 wherein the first group of individuals includes health care providers.

11. The method of claim 10 wherein the first type of data includes health information relating to the patient.

12. The method of claim 11 wherein the second group of individuals includes billing personnel.

13. The method of claim 12 wherein the second type of data includes account information relating to the patient.

14. The method of claim 13 wherein under the access rules the second group of individuals is denied access to the first type of data.

15. The method of claim 1 wherein the first group of individuals includes the selected entity.

16. The method of claim 1 wherein the first group of individuals does not include the selected entity.

17. The method of claim 1 wherein the threshold event relates to an amount of money owed by the patient.

18. The method of claim 1 wherein the threshold event relates to a medical condition of the patient.

19. A tangible computer readable medium storing computer executable instructions for performing a computer implemented method, the method comprising:
   storing records including types of data concerning a patient;
   receiving access rules to selectively control electronic access to the types of data, the access rules determined by the patient;
   controlling access to the types of data by applying the access rules determined by the patient;
   providing to a first group of individuals access to a first type of data concerning the patient according to the access rules determined by the patient;
   providing to a second group of individuals access to a second type of data concerning the patient according to the access rules determined by the patient;
   receiving an indication about a threshold event relating to the patient;
   determining occurrence of the threshold event by comparing a numerical value indicative of a condition of the patient with a threshold value associated with the threshold event;
   providing a notification to an entity selected by the patient in response to the occurrence of the threshold event, wherein the selected entity is not the patient, the threshold event and the notification relating to the first type of data; and
   withholding the notification from the second group of individuals.

20. A system comprising:
   at least one processor; and
   a memory storing instructions configured to instruct the at least one processor to perform:
   storing records including types of data concerning a patient;
   receiving access rules to selectively control electronic access to the types of data, the access rules determined by the patient;
   controlling access to the types of data by applying the access rules determined by the patient;
   providing to a first group of individuals access to a first type of data concerning the patient according to the access rules determined by the patient;
   providing to a second group of individuals access to a second type of data concerning the patient according to the access rules determined by the patient;
   receiving an indication about a threshold event relating to the patient;
   determining occurrence of the threshold event by comparing a numerical value associated with a condition of the patient with a threshold value indicative of the threshold event;
   providing a notification to an entity selected by the patient in response to the occurrence of the threshold event, wherein the selected entity is not the patient, the threshold event and the notification relating to the first type of data; and
   withholding the notification from the second group of individuals.

* * * * *